(12) United States Patent
Demharter

(10) Patent No.: US 8,019,403 B2
(45) Date of Patent: Sep. 13, 2011

(54) MOBILE RADIO TRANSMISSION UNIT

(75) Inventor: Nikolaus Demharter, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 767 days.

(21) Appl. No.: 12/075,723

(22) Filed: Mar. 13, 2008

(65) Prior Publication Data

US 2008/0234557 A1 Sep. 25, 2008

(30) Foreign Application Priority Data

Mar. 22, 2007 (DE) .......................... 10 2007 013 770

(51) Int. Cl.
*A61B 5/05* (2006.01)
(52) U.S. Cl. ........................................ 600/409; 455/423
(58) Field of Classification Search .................... 455/423
See application file for complete search history.

(56) References Cited

U.S. PATENT DOCUMENTS

| | | | |
|---|---|---|---|
| 4,887,609 A * | 12/1989 | Cole, Jr. ........................ | 600/509 |
| 5,629,622 A | 5/1997 | Scampini | |
| 6,239,724 B1 | 5/2001 | Doron et al. | |
| 6,711,434 B2 | 3/2004 | Kramer et al. | |
| 6,937,136 B2 | 8/2005 | Greenwood et al. | |
| 2001/0047130 A1 * | 11/2001 | Walsh .......................... | 600/407 |
| 2002/0033752 A1 | 3/2002 | Greenwood et al. | |
| 2002/0077560 A1 | 6/2002 | Kramer et al. | |
| 2004/0116769 A1 * | 6/2004 | Jassawalla et al. ............. | 600/16 |
| 2008/0129486 A1 | 6/2008 | Jeckelmann et al. | |

FOREIGN PATENT DOCUMENTS

| | | |
|---|---|---|
| DE | 196 26 596 A1 | 1/1997 |
| DE | 100 47 365 B4 | 7/2005 |
| DE | 601 07 512 T2 | 12/2005 |
| WO | 2006114297 A1 | 11/2006 |

* cited by examiner

*Primary Examiner* — Rafael Pérez-Gutiérrez
*Assistant Examiner* — Marcos Batista

(57) ABSTRACT

The invention relates to a mobile radio transmission unit for transferring data to a control and/or signal processing unit. According to the invention, provision is made for a mobile radio transmission unit for transferring data to a control or a signal processing unit, comprising a sensor arrangement for determining at least one component of a surrounding magnetic field. The sensor arrangement is connected to a monitoring entity which, from the at least one component, ascertains a variable that characterizes the surrounding magnetic field and prevents a transmission by an antenna of the radio transmission unit if the characteristic variable is below a threshold value.

12 Claims, 3 Drawing Sheets

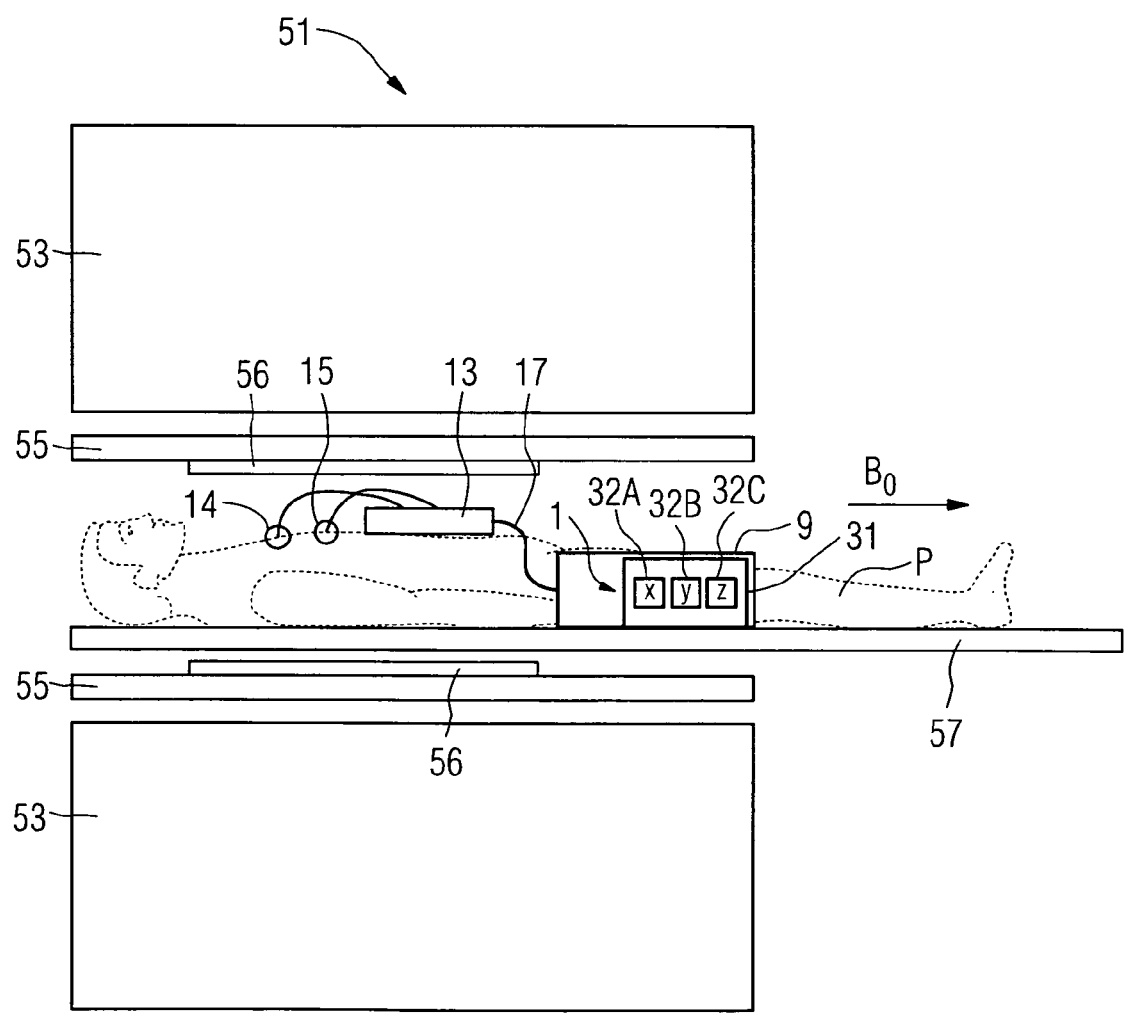

MOBILE RADIO TRANSMISSION UNIT

CROSS REFERENCE TO RELATED APPLICATIONS

This application claims priority of German application No. 10 2007 013 770.4 filed Mar. 22, 2007, which is incorporated by reference herein in its entirety.

FIELD OF THE INVENTION

The invention relates to a mobile radio transmission unit for transferring data to a control and/or signal processing unit.

BACKGROUND OF THE INVENTION

Wireless devices, which transfer data e.g. by means of radio, are increasingly used in all possible fields of everyday life. In industry and medicine also, the conventional data transfer by means of cables is increasingly being replaced by wireless techniques.

In industry and medicine, the increasing number of radio participants, e.g. including Bluetooth devices, typically transmit over a limited range but can also disrupt each other when operated concurrently. It is therefore desirable to prevent these devices from transmitting when this is not applicable. Mechanical contacts which are activated e.g. via a plug connector and prevent transmission by the devices are known for this purpose. However, these plug connectors can easily be lost or not plugged in due to forgetfulness.

A radio solution for transferring data is suitable in connection with magnetic resonance techniques, in particular, since electrical data lines are disrupted by the electromagnetic fields which exist in magnetic resonance devices, and can also themselves disrupt the recordings. The magnetic resonance technique (the abbreviation MR represents magnetic resonance in the following) is a known technique by means of which images of the interior of an examination object can be generated. Expressed simply, for this purpose, the examination object is positioned in an MR device in a comparatively strong static homogenous primary magnetic field (field strengths of 0.2 to 7 Tesla and higher), such that its nuclear spins are aligned along the primary magnetic field. For the purpose of triggering nuclear spin resonances, high-frequency excitation pulses are beamed into the examination object, the nuclear spin resonances are measured and MR images are reconstructed on the basis of these. For location coding of the measured data, rapidly switched magnetic gradient fields are superimposed on the primary magnetic field.

A mobile radio transmission unit for transferring physiological data is disclosed in DE 100 47 365 B4 (corresponds to U.S. Pat. No. 6,711,434). This document discloses a physiological sensor system which is designed in such a way that it can record measurement signals, in particular in a magnetic resonance device. However, the operation of this physiological sensor system in connection with an MR device presents particular requirements, since the strong magnetic fields and electromagnetic alternating fields of the MR device influence magnetic and electrically conductive objects by e.g. inducing currents and/or opposing fields or by pulling magnetic objects towards the magnets of the MR device. As a result, in particular the operation of electrical units can be disrupted and e.g. lead to false results.

One possibility for avoiding such undesired effects is to equip the affected objects with a screen against the fields of the MR device. In this way, devices having an electronic system can also be operated without disruption within the electromagnetic fields of an MR device.

Another possibility is to ensure that objects which can be affected are kept at an adequate distance from the MR device. This provides a solution in a simple manner, since the magnetic field decreases rapidly as the distance from the MR device increases.

For this purpose, a magnetic field detection system for the protection of connected electronic devices is disclosed in DE 196 26 596 A1 (corresponds to U.S. Pat. No. 5,629,622 A), for example, and emits warning signals when the connected electrical device comes too close to an MR device.

Such a solution is not viable in every case, however, since exposing certain electronic devices or units to strong magnetic fields is not always avoidable or might even be necessary.

SUMMARY OF THE INVENTION

The present invention therefore addresses the problem of preventing any disruption of other radio participants by such devices or units.

The problem is solved according to the invention by a mobile radio transmission unit in accordance with the independent claim. Further advantageous embodiments are characterized by the features in the dependent claims.

According to the invention, provision is made for a mobile radio transmission unit for transferring data to a control and/or signal processing unit, comprising a sensor arrangement for determining at least one component of a surrounding magnetic field, wherein the sensor arrangement is connected to a monitoring entity which, from the at least one component, ascertains a variable that characterizes the surrounding magnetic field and prevents a transmission by an antenna of the radio transmission unit if the characteristic variable is below a threshold value.

In particular, the magnetic field of an MR device and also its flux leakage field are significantly greater than the earth's magnetic field or other naturally occurring magnetic fields. By preventing the transmission of the radio transmission unit if the ascertained characteristic variable of the surrounding magnetic field lies below a predetermined threshold value, it is ensured that the mobile radio transmission unit only transmits where its transmission function is desired, e.g. in the primary magnetic field or flux leakage field of an MR device. The reliability is thus increased in a simple manner, and a maximally disruption-free operation of other devices which transmit by means of radio is allowed.

In a further embodiment, the sensor arrangement comprises at least a magnetic sensor, in particular a Hall sensor. Also conceivable are sensors comprising magneto-resistive elements, saturation inductivity elements, flux gate devices or optical fiber sensors which use magneto-optical materials. Magnetic sensors allow components of even static magnetic fields to be determined in a simple manner.

The mobile radio transmission unit is advantageously designed such that it is MR-compatible. In other words, the materials and/or the structural design of the mobile radio transmission unit ensure disruption-free operation of an MR device and also disruption-free operation of the mobile radio transmission unit in an MR device. In addition, the mobile radio transmission unit comprises a suitable screening apparatus and/or is manufactured from non-magnetic materials.

In a further embodiment, the mobile radio transmission unit comprises a signal handling unit for minimizing or preventing disruptions of the determination of the component of the surrounding magnetic field. By means of signal handling, which is based on e.g. low-pass filters, time-relative averaging over a predetermined time period and/or other smoothing methods, it is easily possible to equalize disruptions of the magnetic field recognition, said disruptions being caused by moving the mobile radio transmission unit or by the electromagnetic alternating fields of an MR device.

An embodiment is advantageous in which the mobile radio transmission unit is designed for transmitting in the ISM band. The ISM band (Industrial, Scientific, and Medical band) consists of frequency ranges for high-frequency transmission devices which are not subject to governmental regulation and can effectively be used freely. It is therefore possible to make extensive use of standard parts in the case of this embodiment.

In a further advantageous embodiment, the mobile radio transmission unit is connected to at least one measuring sensor for recording electrical measurement signals in an environment which affects the recording, in particular in an MR device, or for recording non-electrical measurement signals. This means that a multiplicity of measurement signals, which are used e.g. for monitoring and/or capturing the life signs of a patient and/or environmental conditions, can be transferred via the mobile radio transmission unit.

BRIEF DESCRIPTION OF THE DRAWINGS

Further advantages and details of the present invention are derived from the exemplary embodiments which are described below and with reference to the drawings. The stated examples do not represent any restriction of the invention.

FIG. 3 shows a schematic diagram of an MR device comprising a measuring sensor system as per FIG. 1.

DETAILED DESCRIPTION OF THE INVENTION

Figure 1:
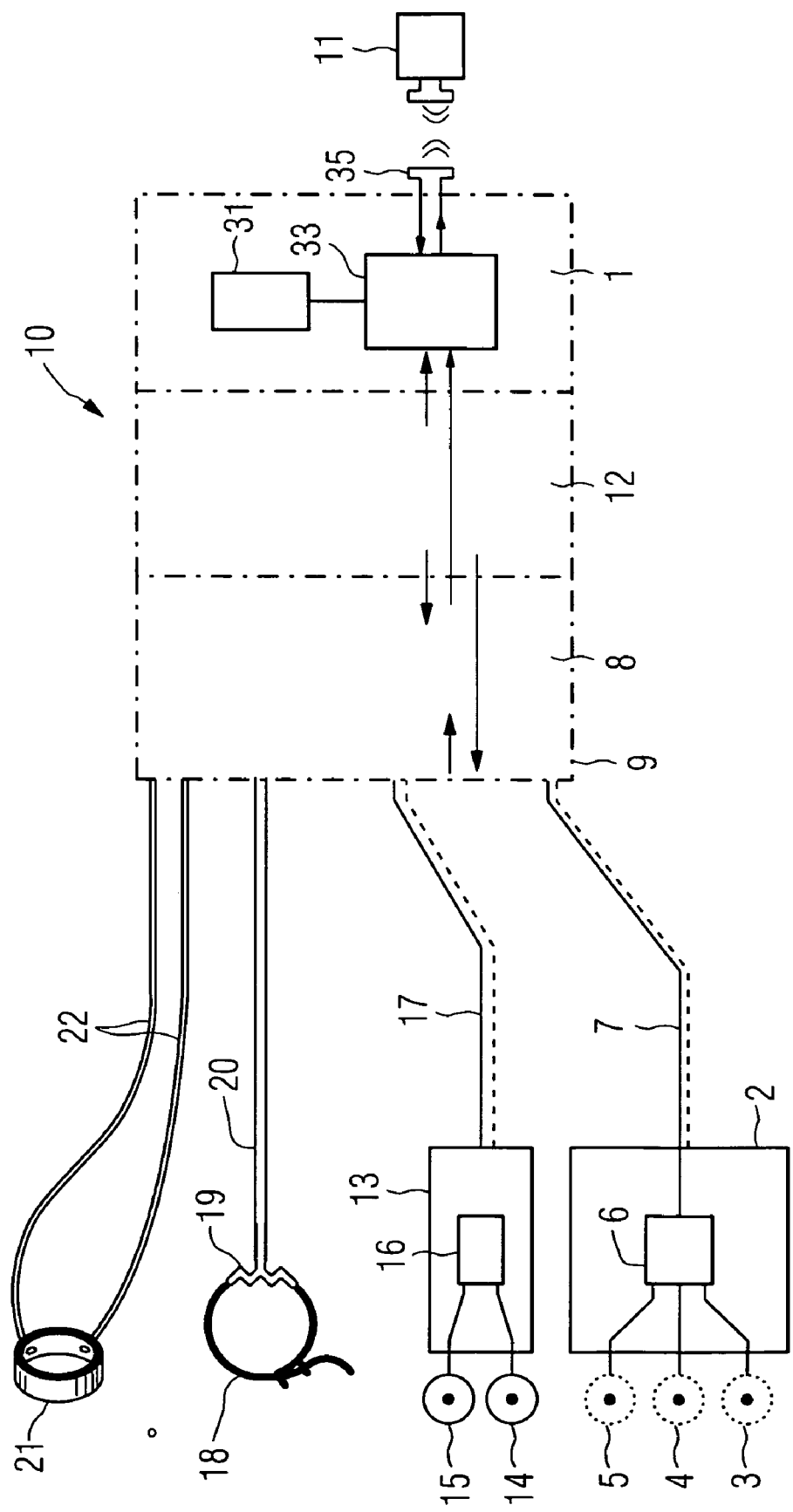
FIG. 1 shows a schematic illustration of a measuring sensor system comprising a mobile radio transmission unit according to the invention.

FIG. 1 shows a schematic illustration of a measuring sensor system 10 with a mobile radio transmission unit 1 according to the invention. In the exemplary form which is illustrated, the measuring sensor system comprises a first housing 2, at which three electrodes 3, 4, 5 are arranged in the example shown and are designed e.g. for recording an ECG. A signal amplification entity 6 which amplifies the signals that are supplied via the electrodes 3, 4, 5 is also arranged in the first housing 2. The measurement signals are passed via a screened or twisted cable connection 7 to a signal conversion module 8 which is arranged in a second screened housing 9. There, the signals are converted and then passed via the radio transmission unit 1 to an external signal processing and/or control device 11. According to the invention, radio transmission unit 1 comprises a sensor arrangement 31 which is connected to a monitoring entity 33, this in turn being connected to an antenna 35. Details of the functionality of the radio transmission unit are given in FIG. 2 and the associated description. A power supply 12 which supplies power to the entire measuring sensor system 10 is additionally arranged in the second housing 9.

In addition to the first housing 2, provision can be made for further first housings. In the example shown, two electrodes 14, 15 are arranged at a second first housing 13. These are designed e.g. for recording EEG measurements. However, provision can be made for more electrodes. A signal amplification entity 16 which amplifies the signals locally, i.e. directly at the measurement location, is also arranged in this first housing 13. The measurement signals are also passed to the signal conversion module 8 via a twisted or screened cable connection 17 and prepared accordingly.

Also attached to the second screened housing 9 is a further sensor element 18, this being a flexible chest ring in the exemplary embodiment which is shown, by means of which the respiration of a patient can be recorded. This comprises a compressible volume of air 19 which is compressed or expanded accordingly as the thorax rises and falls. The varying pressure is passed to a corresponding sensor in the signal conversion module 8 via a pneumatic connection line 20. Also connected to the second housing 9 is a second sensor element 21 in the form of a finger ring, by means of which the peripheral pulse of the patient can be measured by IR absorption of the blood. The recorded non-electrical measurement information (the information which is recorded by means of the sensor element 18 is also non-electrical measurement information) is passed to a corresponding sensor element in the signal conversion module 8 via optical fiber lines 22 in this case. Possible structural designs of a signal conversion module are known from the prior art. By way of example, reference is again made to DE 100 47 365 B4 as cited in the introduction. Provision can also be made for further measuring sensors (not shown) which measure e.g. a local loudness level or other environmental conditions. These can be valuable for a diagnosis. For example, a sudden loudness increase indicates a sudden pulse increase.

In the example which is illustrated, the entire measuring sensor system 10 is mobile and can be placed in an MR device if necessary, e.g. with a patient whose physiological data is to be captured and transmitted (FIG. 3).

Figure 2:
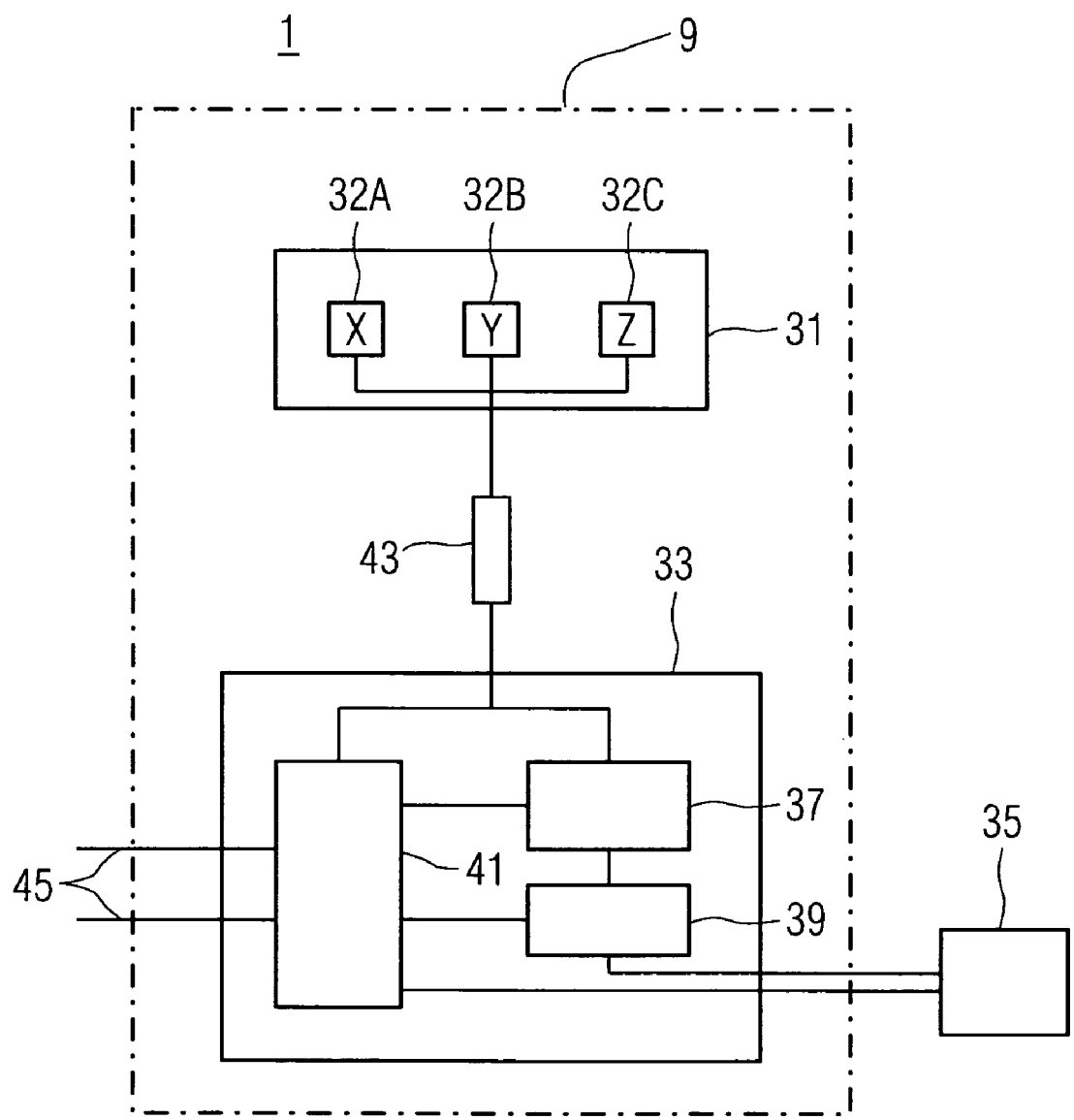
FIG. 2 shows a schematic diagram of an advantageous embodiment of a mobile radio transmission unit according to the invention.

FIG. 2 shows a schematic diagram of an advantageous embodiment of a mobile radio transmission unit according to the invention. A sensor arrangement 31 is arranged in a screened housing 9. The sensor arrangement 31 comprises at least one magnetic sensor 32A. Two further magnetic sensors 32B, 32C are illustrated in the example. Each of the sensors 32A, 32B, 32C measures one magnetic field component in one of three relatively perpendicular directions x,y,z. The sensors 32A, 32B, 32C of the sensor arrangement 31 are connected to a monitoring entity 33 in order that the measured signals can be transferred. This connection advantageously comprises a signal handling unit 43, e.g. a low-pass filter, for minimizing or preventing disruptions of the determination of the components of the surrounding magnetic field. The signal handling unit 43 can also be part of the monitoring unit 33.

The monitoring unit 33 comprises a transmit/receive unit 41, to which the components $K_x$, $K_y$, $K_z$ measured by the sensors 32A, 32B, 32C are transferred. In addition, the components $K_x$, $K_y$, $K_z$ measured by the sensors 32A, 32B, 32C are transferred to a processing unit 37 of the monitoring unit 33, where they are used for determining a characteristic variable of the surrounding magnetic field. The characteristic variable is e.g. the magnitude of the measured magnetic field vector. In the example having the three sensors 32A, 32B, 32C in the directions x, y, z, therefore, this is the root of the squares of the three measured components $\sqrt{K_x^2+K_y^2+K_z^2}$. A magnitude of a magnetic field vector can also be determined analogously as a characteristic variable from only two or one measured component(s).

The processing unit 37 transfers the determined characteristic variable to the transmit/receive unit 41 and to a comparison unit 39. The transmit/receive unit 41 converts the measured components and/or the characteristic variable of the surrounding magnetic field into data which can be transferred by the antenna 35. In the comparison unit 39, the determined characteristic variable is compared with a threshold value. If the characteristic variable is lower than the threshold value, the comparison unit 39 prevents a transmission by the antenna 35, e.g. by transmitting a corresponding control signal to the antenna 35 of the radio transmission unit 1. As a result, the antenna 35 cannot transmit the data from the transmit/receive unit 41. For the purpose of increasing the reliability, a specific control signal can also be provided for enabling the transmission by the antenna 35. In this case, the comparison unit refrains from transferring this enabling signal to the antenna in order to prevent the transmission. In a further embodiment, both a control signal for disabling and a control signal for enabling the antenna 35 can be provided.

The antenna 35 is also designed for receiving data. In particular, from the control and/or signal processing unit 11, it can receive the threshold value which is required for the comparison in the comparison unit 39 and transfer it to the transmit/receive unit 41. In order that the comparison unit 39 has access to the current threshold value, it is connected to the transmit/receive unit 41. This offers advantages in particular if the mobile radio transmission unit 1 is used in various MR devices having possibly widely differing primary magnetic fields. The threshold value is selected as required, such that the mobile radio transmission unit 1 can still transmit in the flux leakage field of the MR device, i.e. in the immediate vicinity of the MR device, or only directly within the primary magnetic field inside the MR device.

The above described functional units comprising sensor arrangement 31 and monitoring entity 33 can also be integrated in a single part. Magnetic sensors 32A,32B,32C with integrated threshold value recognition are known, e.g. in the form of digital Hall sensors or "on-off" sensors. They output a constant current as soon as e.g. the magnetic field strength reaches a threshold value, wherein this can also be pre-programmed in particular.

Further connections 45 for transferring signals and/or power connect the transmit/receive unit 41 to e.g. the signal conversion module 8 and/or the power supply 12 from FIG. 1.

FIG. 3 shows an exemplary MR device 51 in a highly simplified illustration which is not to scale. A primary magnet 53 generates the primary magnetic field $B_0$ (arrow in FIG. 3) which is required for the MR examination. Using gradient coils 55, during a measurement, magnetic gradient fields are beamed in for selective layer excitation and for location coding of the measured signal. The excitation of the nuclear spin of a patient P takes place using magnetic high-frequency excitation pulses which are beamed in via MR coils 56. The signals which are output by the excited nuclear spins are received again by MR coils 56. The measuring sensor system 10 can be arranged at least partially on the patient P or also beside the patient P on the couch 57. By way of example, FIG. 3 shows the measuring sensors 14 and 15 of the measuring sensor system, wherein these are connected to the first screened housing 13 which is in turn connected to the second screened housing 9, in which the mobile radio transmission unit 1 is arranged.

Assuming the mobile radio transmission unit 1 comprises three magnetic sensors 32A,32B,32C, each of which measures a magnetic field component $K_x$, $K_y$, $K_z$ in one of three relatively perpendicular directions x,y,z, the sensor arrangement 31 always detects the whole magnetic field in each position of the mobile radio transmission unit 1. The transmission by the antenna 35 is therefore only prevented if the mobile radio transmission unit 1 is situated outside of a magnetic field having at least the strength of the threshold value.

In order to economize current consumption, weight and space, for example, it is also possible to utilize fewer than three magnetic sensors 32A,32B,32C. However, the alignment of the mobile radio transmission unit 1 in the MR device 51 must then be considered:

Assuming the mobile radio transmission unit 1 comprises two magnetic sensors 32A,32B, each of which measures a magnetic field component in one of two relatively perpendicular directions x,y, the primary magnetic field of the MR device 51 is only correctly determined if the primary magnetic field direction ($B_0$ direction) lies in the plane which extends through the two measurement directions x and y. In order to prevent transmission by such a mobile radio transmission unit 1, it is sufficient to rotate the second screened housing 9, and hence the sensor arrangement 31 which is arranged in the mobile radio transmission unit 1, such that the magnetic sensors 32A,32B measure in two directions which cover a plane that no longer fully recognizes the magnetic field component in $B_0$ direction, e.g. a plane which lies perpendicular to the $B_0$ direction. Depending on the selected threshold value, it can already be sufficient to rotate the extended measurement plane by a specific angle away from the $B_0$ direction, in order to prevent a transmission by the mobile radio transmission unit 1. In the case of a threshold value of 77% of the primary magnetic field, for example, a transmission by the mobile radio transmission unit 1 is prevented if it was rotated such that the magnetic sensors 32A, 32B measure magnetic field components in a plane whose normal vector was tilted by an angle α, where α is between 50° and 130°, relative to the $B_0$ direction, even if it is situated in the primary magnetic field of the MR device 51.

Assuming the mobile radio transmission unit 1 comprises only one magnetic sensor 32A, the primary magnetic field of the MR device 51 is only correctly recognized if the single magnetic sensor 32A accurately measures the magnetic field component in z direction, i.e. the primary magnetic field direction. In order to prevent a transmission by such a mobile radio transmission unit 1, it is sufficient to rotate the second screened housing 9, and hence the sensor arrangement 31 which is arranged in the mobile radio transmission unit 1, such that the magnetic sensor 32A measures in a direction which no longer fully recognizes the magnetic field component in $B_0$ direction, e.g. in a direction which is perpendicular to the $B_0$ direction. As in the case of two sensors 32A,32B, depending on a selected threshold value, even a rotation of the measurement direction by a specific angle away from the z direction can already suffice to prevent a transmission by the mobile radio transmission unit 1. In the example of a threshold value of 77% of the primary magnetic field, therefore, a tilting of the measurement direction by an angle α, where α is between 40° and 140°, relative to the $B_0$ direction is sufficient to prevent a transmission by the mobile radio transmission unit 1, even if it is situation in the primary magnetic field of the MR device 51.

In particular if a plurality of radio transmission units are to be used e.g. alternately during an examination, it is advantageous to allow only a single radio transmission unit to transmit in each case, since a plurality of transmitting radio transmission units can disrupt each other. In the embodiments having one or two magnetic sensors 32, a transmission by a radio transmission unit can easily be prevented or enabled by rotating or tilting the radio transmission unit without having to remove the radio transmission unit from the MR device. This saves time and effort. Even if no access to the radio transmission units is possible during the examination, alternating transmission by the radio transmission units can be achieved by transferring higher or suitable threshold values to the relevant radio transmission unit in each case. This is also possible for the embodiment having three magnetic sensors.

The invention claimed is:

1. A mobile radio transmission unit for transferring data to a control unit of a device, comprising:
    a sensor arrangement that measures a component of a surrounding magnetic field of the device; and
    a monitoring unit that comprises:
        a transmit and receive unit that receives the measured component,
        a processing unit that determines a characteristic variable of the surrounding magnetic field based on the measured component, and
        a comparison unit that compares the characteristic variable with a threshold value to prevent transferring data to the control unit if the characteristic variable is lower than the threshold value, wherein the mobile radio transmission unit rotates or tilts for transferring or preventing transferring the data to the control unit without removing the mobile radio transmission unit from the device.

2. The mobile radio transmission unit as claimed in claim 1, wherein the sensor arrangement comprises a magnetic sensor.

3. The mobile radio transmission unit as claimed in claim 2, wherein the magnetic sensor is a Hall sensor.

4. The mobile radio transmission unit as claimed in claim 1, wherein the mobile radio transmission unit is MR-compatible.

5. The mobile radio transmission unit as claimed in claim 1, further comprising a signal handling unit that minimizes or prevents disruption of measuring the component of the surrounding magnetic field.

6. The mobile radio transmission unit as claimed in claim 1, wherein the data is transferred in ISM band.

7. The mobile radio transmission unit as claimed in claim 1, wherein the mobile radio transmission unit is connected to a measuring sensor that records electrical measurement signal or non-electrical measurement signal in the device.

8. The mobile radio transmission unit as claimed in claim 7, wherein the measuring sensor is MR-compatible.

9. The mobile radio transmission unit as claimed in claim 7, wherein the measuring sensor records physiological data of a patient examined by the device.

10. The mobile radio transmission unit as claimed in claim 1, wherein the comparison unit transmits a control signal to an antenna of the mobile radio transmission unit based on the comparison result.

11. The mobile radio transmission unit as claimed in claim 10, wherein the antenna transfers or prevents transferring the data to the control unit based on the control signal.

12. The mobile radio transmission unit as claimed in claim 1, wherein the device is a MR device.

* * * * *